April 19, 1955 H. C. SWIM Plant Pat. 1,381
ROSE PLANT
Filed June 29, 1953
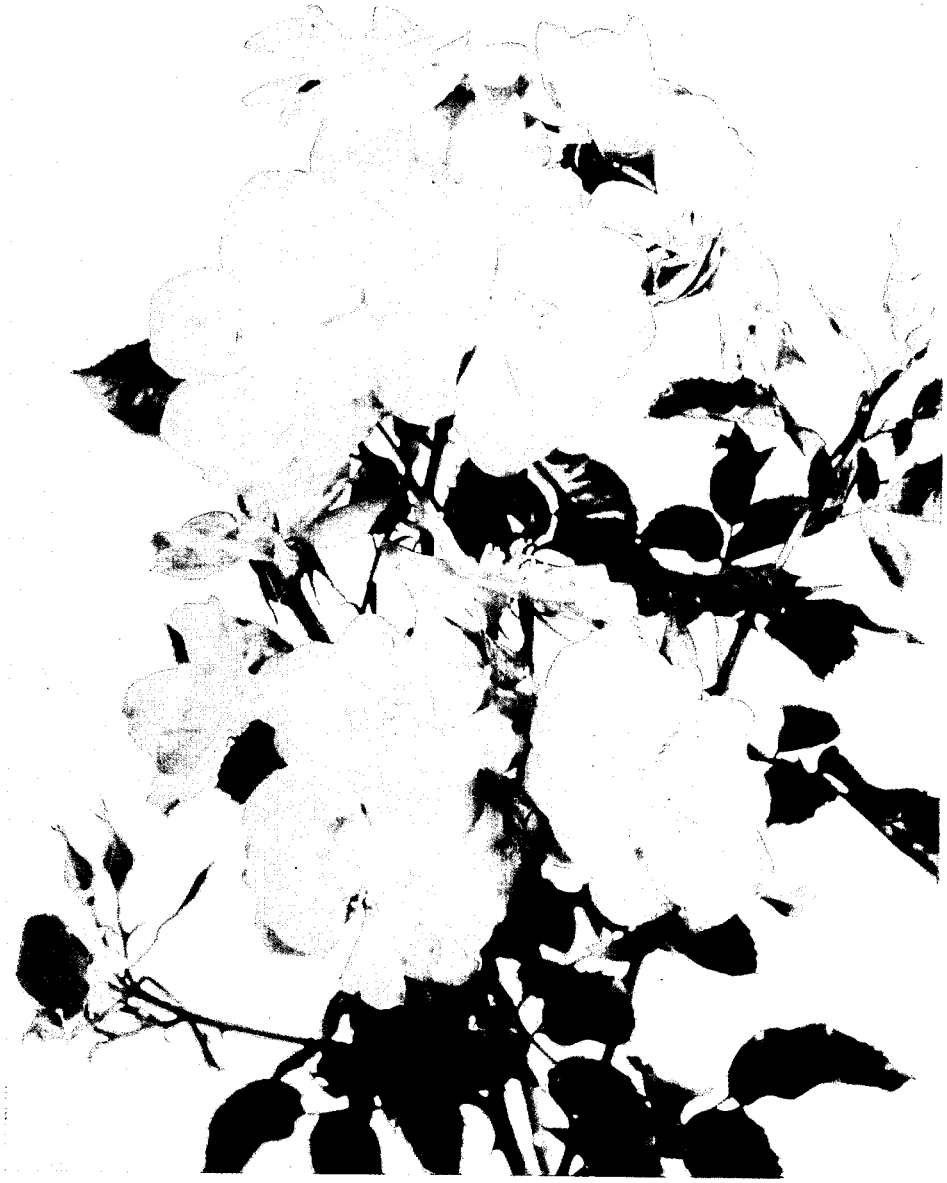
Inventor
H. C. Swim
By: Robb & Robb
Attorneys.

United States Patent Office

Plant Pat. 1,381
Patented Apr. 19, 1955

1,381

ROSE PLANT

Herbert C. Swim, Ontario, Calif., assignor to Armstrong Nurseries, Inc., Ontario, Calif., a corporation of California Application June 29, 1953, Serial No. 364,976

1 Claim. (Cl. 47—61)

The present invention relates to a new and distinct variety of rose plant of the hybrid polyantha class, which was originated by me by crossing the variety "Minna Kordes," better known in the United States as "World's Fair" (Plant Patent No. 362) with the variety "Pinocchio" (Plant Patent No. 484).

The primary objective in making this cross was to produce a new variety of rose plant which combines the best characteristics of the two parent varieties. This objective was fully achieved, as evidenced by the fact that my new rose variety is endowed with the following unique combination of outstanding characteristics:

(1) The bushy, compact and vigorous habits of growth of the plant, the vigor being substantially equal to that of the seed parent "World's Fair";

(2) The many-flowered cluster habit of bloom, which is a characteristic trait of "Pinocchio," but with substantially more flowers per cluster than in either parent;

(3) The nearly single petalage of the flowers, with fewer petals than the flowers of either parent; and (4) The medium shade of red color of the flowers, approaching that of "World's Fair," but lighter and somewhat brighter than the latter.

In comparison with its seed parent "World's Fair," the blooms of my new variety are produced in many-flowered clusters, with substantially more flowers per cluster than are produced by "World's Fair"; the flower size and petal size of the new variety are somewhat smaller than those of "World's Fair"; the flowers of the new variety are nearly single and have from 8 to 10 petals, whereas the flowers of "World's Fair" are semi-double and have from 18 to 20 petals; and the flower color of my new variety is a medium shade of red, whereas that of "World's Fair" is a deep shade of red.

As compared with its pollen parent "Pinocchio," the flower color of my new variety is a medium shade of red, whereas that of "Pinocchio" is pink suffused salmon; the flowers of the new variety are nearly single and have from 8 to 10 petals, whereas those of "Pinocchio" are double and have about 30 petals; the blooms of my new variety are produced in many-flowered clusters, with substantially more flowers per cluster than are produced by "Pinocchio"; the flower size of the new variety is large for its class, ranging from 2¾ to 3¼ inches in diameter, whereas the average flower size of "Pinocchio" is about 2 inches in diameter; and the foliage of my new variety is abundant, whereas that of "Pinocchio" is below normal in quantity.

Asexual reproduction of my new variety by budding at Ontario, California, shows that the foregoing characteristics and distinctions come true to form and are established and transmitted through succeeding propagations.

The accompanying drawing shows typical specimens of the flowers, foliage and stems of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter identified as "Wilson") and with Ridgway's Color Standards and Nomenclature (hereinafter identified as "Ridgway"):

Type: Bush; outdoor; seedling; for garden decoration.
Class: Hybrid polyantha.

Breeding: Seedling.
*Seed parent.*—"World's Fair."
*Pollen parent.*—"Pinocchio."
Propagation: Holds its distinguishing characteristics through succeeding propagations by budding.

FLOWER

Locality where grown and observed: Ontario, California.
Flowers borne: Usually several to stem; in regular, rounded cluster; on strong, medium length stems.
Quantity of bloom: Very abundant, outdoors.
Continuity: Nearly continuous during growing season.
Fragrance: None to slight.
Bud:
*Peduncle.*—Short to average length; average caliper; erect; usually smooth; some gland-tipped cilia and few prickles. Color—between Courge Green, Plate XVII (Ridgway) and Biscay Green, Plate XVII (Ridgway), shaded with between Indian Red, Plate XXVII (Ridgway) and Prussian Red, Plate XXVII (Ridgway) on side exposed to the sun.
*Before calyx breaks.* — Size — medium. Form—medium length; ovoid; with foliaceous appendages; some tomentum and some gland-tipped cilia on the surface of the bud; usually without stout, much-cut foliaceous parts extending beyond the tip of the bud.
*As calyx breaks.*—Color—between Cardinal Red, Plate 822, page 168 (Wilson) and Cardinal Red, Plate 822/1, page 168 (Wilson).
*Sepals.*—Inner surface—With fine, woolly tomentum. Margins—alternate sepals lined with fine, woolly tomentum; others lined with stipitate glands.
*As first petal opens.*—Size—average. Form—medium length; ovoid. Color: Outside—between Cardinal Red, Plate 822/2, page 168 (Wilson) and Cardinal Red, Plate 822/3, page 168 (Wilson); small area at base of petal near attachment between Canary Yellow, Plate 2/2, page 2 (Wilson) and Canary Yellow, Plate 2/3, page 2 (Wilson). Inside—near Currant Red, Plate 821/2, page 167 (Wilson); area near attachment between Cherry, Plate 722/1, page 157 (Wilson) and Cherry, Plate 722/2, page 157 (Wilson), and a small area at attachment between Canary Yellow, Plate 2/2, page 2 (Wilson) and Canary Yellow, Plate 2/3, page 2 (Wilson).
*Opening.*—Opens up well; is not retarded from opening by cold, hot, wet or dry weather.
Bloom:
*Size (when fully open).*—Average to large; 2¾ to 3¼ inches.
*Petalage.*—Single to semi-double; from 8 to 10 petals, plus 1 to 2 petaloids; arranged regularly.
*Form.*—Open at first; becoming flat to open; petals being at first cupped, with lateral margins curved inward; an occasional petal has lateral margins reflexed for ⅓ to ½ of upper portion of the petal; apex reflexed for ⅛ of petal on an occasional petal; becoming later at maturity flat-cupped, with most of the petals having lateral margins curved slightly inward; an occasional petal with lateral margins reflexed; some petals with apex reflexed ⅛ to ¼ of petal.
Petals:
*Texture.*—Medium to thick; leathery; with inside velvety and outside satiny.
*Shape.*—Broadly obovate, with apex somewhat flat; rarely with 1 or 2 notches.

This description of a newly opened flower was made from a rose grown outdoors in the month of November, at Ontario, California:

Color:
*Petal.*—Outside surface—near Cardinal Red, Plate 822/3, page 168 (Wilson); small area at base of petal near attachment near Canary Yellow, Plate 2/3, page 2 (Wilson). Inside surface—near Currant Red, Plate 821/3, page 167 (Wilson); an area near base of petal between Cherry, Plate 722/2, page 157 (Wilson) and Cherry, Plate 722/3, page 157 (Wilson); small area at attachment at base near Canary Yellow, Plate 2/3, page 2 (Wilson).

This description was made from a rose that was open for three days outdoors in the month of December, at Ontario, California:

Color:

*Petal.*—Outside surface—between Cardinal Red, Plate 822/2, page 168 (Wilson) and Cardinal Red, Plate 822/3, page 168 (Wilson); small area at base of petal near attachment near Canary Yellow, Plate 2/3, page 2 (Wilson). Inside surface—between Cherry Red, Plate 722, page 157 (Wilson) and Currant Red, Plate 821/3, page 167 (Wilson); overlaid somewhat with near Chrysanthemum Crimson, Plate 824, page 169 (Wilson); small area at base near attachment near Canary Yellow, Plate 2/3, page 2 (Wilson).

General color effect:

*Newly opened flower.*—Between Currant Red, Plate 821/2, page 167 (Wilson) and Cherry, Plate 722/1, page 157 (Wilson); small area at base of petal at attachment near Canary Yellow, Plate 2/3, page 2 (Wilson).

*Three days open.*—Between Currant Red, Plate 821/1, page 167 (Wilson) and Cardinal Red, Plate 822/1, page 168 (Wilson); small area at base near attachment near Canary Yellow, Plate 2/3, page 2 (Wilson).

Behavior: Drop off cleanly; not particularly affected by cold, hot, wet or dry weather.

Flower longevity: On bush in garden—4 to 5 days in December. Cut flowers grown outdoors kept at living-room temperatures—4 to 5 days in December.

REPRODUCTIVE ORGANS

Stamens: Average number to many; arranged regularly about pistils.

Filaments: Medium length; 5 to 9 mm. in length; most with anthers.

*Color.*—Between Sulphur Yellow, Plate 1/2, page 1 (Wilson) and Canary Yellow, Plate 2/1, page 2 (Wilson).

Anthers: Medium size; all open approximately at once.

*Color.*—Upper side—margins between Buttercup Yellow, Plate 5/2, page 5 (Wilson) and Indian Yellow, Plate 6/2, page 6 (Wilson); remainder near Mimosa Yellow, Plate 602/3, page 143 (Wilson). Under side—margins between Buttercup Yellow, Plate 5/2, page 5 (Wilson) and Indian Yellow, Plate 6/2, page 6 (Wilson); remainder near Mimosa Yellow, Plate 602/3, page 143 (Wilson).

Pollen: Abundant.

*Color.*—Between Indian Yellow, Plate 6/2, page 6 (Wilson) and Saffron Yellow, Plate 7/2, page 7 (Wilson).

Pistils: Average number; approximately 50 in number.

Styles: Even; average length; thin to average caliper; columnar; 7 to 10 mm. in length.

*Color.*—Near Uranium Green, Plate 63/3, page 63 (Wilson); upper portion overlaid somewhat with near Carmine, Plate 21/2, page 21 (Wilson).

Stigma: Color—near Primrose Yellow, Plate 601/1, page 65 (Wilson).

Ovaries: Usually all enclosed in calyx.

Hips: Short to average length; ovoid to globular; smooth; walls thick and fleshy.

*Color (mature).*—Between Saturn Red, Plate 13, page 13 (Wilson) and Nasturtium Red, Plate 14/1, page 14 (Wilson).

Sepals: Permanent; medium length; recurved.

*Color.*—Inside—between Courge Green, Plate XVII (Ridgway) and Biscay Green, Plate XVII (Ridgway); sometimes overlaid with near Mineral Red, Plate XXVII (Ridgway); masked by white, woolly tomentum. Outside—near Biscay Green, Plate XVII (Ridgway); sometimes overlaid with near Indian Red, Plate XXVII (Ridgway).

Seeds: Very few; medium size; 2 to 5 in number.

PLANT

Foilage:

*Leaves.*—Compound of usually 5 to 7 leaflets; abundant; medium size; leathery; semi-glossy.

*Leaflets.*—Shape—ovoid, with acute apex and round base. Margin—simply serrate.

*Color.*—Mature: Upper surface—between Deep Dull Yellow Geen, Plate XXXII (1) (Ridgway) and Dark Dull Yellow Green, Plate XXXII (Ridgway). Under surface—between Turtle Green, Plate XXXII (Ridgway) and Chromium Green, Plate XXXII (Ridgway). Young: Upper surface—near Cress Green, Plate XXXI (Ridgway), heavily overlaid with near Dark Mineral Red, Plate XXVII (Ridgway). Under surface—near Mineral Red, Plate XXVII (Ridgway).

*Rachis (the supporting stem of the compound leaf).*—Average size. Upper side—grooved; hairy; with some stipitate glands on edges. Under side—Prickly and with stipitate glands.

*Stipules.*—Medium length; medium width, with medium length points turning out at an angle of more than 45°.

*Disease.*—Average resistance to mildew, as determined by comparison with other varieties grown under comparable cultural conditions at Ontario, California.

Growth:

*Habit.*—Bushy; much-branched; from 3½ to 4 feet tall.

*Growth.*—Very vigorous.

*Canes.*—Medium caliper.

*Main stems.*—Color—between Oil Green, Plate V (Ridgway) and Spinach Green, Plate V (Ridgway). Large prickles—several to many; medium length; hooked downward; with medium length, somewhat narrow base. Color—between Light Drab, Plate XLVI (Ridgway) and Light Grayish Olive, Plate XLVI (Ridgway). Small prickles—few to several. Color—near Light Grayish Olive, Plate XLVI (Ridgway). Hairs—none.

*Branches.*—Color—between Biscay Green, Plate XVII (Ridgway) and Bice Green, Plate XVII (Ridgway). Large Prickles—several to many; medium length; hooked downward; with medium length, somewhat narrow base. Color—between Sayal Brown, Plate XXIX (Ridgway) and Snuff Brown, Plate XXIX (Ridgway). Small prickles—several. Color—near Sayal Brown, Plate XXIX (Ridgway). Hairs—none.

*New shoots.*—Color—near Courge Green, Plate XVII (Ridgway); overlaid somewhat with near Indian Red, Plate XXVII (Ridgway). Large prickles—several to many; medium length; hooked downward; with medium length, somewhat narrow base. Color—near Mineral Red, Plate XXVII (Ridgway.) Small prickles—several. Color—near Mineral Red, Plate XXVII (Ridgway). Hairs—none.

I claim:

A new and distinct variety of rose plant of the hybrid polyantha class, substantially as herein shown and described, characterized particularly as to novelty by its bushy, compact and vigorous habits of growth, by its habit of producing blooms in many-flowered clusters, with substantially more flowers per cluster than those of either parent variety, by the nearly single petalage of its flowers, and by the medium shade of red general color tonality of its flowers, approaching that of the parent variety "World's Fair" (Plant Patent No. 362), but lighter and somewhat brighter than the latter.

No references cited.